United States Patent [19]

Pfeiler et al.

[11] 4,345,158
[45] Aug. 17, 1982

[54] TOMOGRAPHIC APPARATUS FOR THE PRODUCTION OF TRANSVERSE LAYER IMAGES

[75] Inventors: Manfred Pfeiler; Karlheinz Pauli, both of Erlangen, Fed. Rep. of Germany

[73] Assignee: Siemens Aktiengesellschaft, Berlin & Munich, Fed. Rep. of Germany

[21] Appl. No.: 196,530

[22] Filed: Oct. 14, 1980

[30] Foreign Application Priority Data

Oct. 29, 1979 [DE] Fed. Rep. of Germany ....... 2943643

[51] Int. Cl.$^3$ ................................................. A61B 6/00
[52] U.S. Cl. ........................................... 378/5; 378/9; 378/14; 378/19
[58] Field of Search .................................... 250/445 T

[56] References Cited

U.S. PATENT DOCUMENTS 3,971,948 7/1976 Pfeiler et al. ..................... 250/445 T
4,057,725 11/1977 Wagner ........................... 250/445 T
4,149,081 4/1979 Seppi ................................ 250/445 T Primary Examiner—Alfred E. Smith
Assistant Examiner—T. N. Grigsby
Attorney, Agent, or Firm—Hill, Van Santen, Steadman, Chiara & Simpson

[57] ABSTRACT

In an exemplary embodiment, a radiation measuring arrangement has two x-ray tubes of different radiation energy which generate radiation beams penetrating the radiography subject, and also has a radiation receiver which determines the radiation intensity behind the subject. The radiography subject is irradiated from different directions. A computer determines, for every image point, the attenuation coefficient for every radiation energy and determines therefrom the mean ordinal number and the density. The radiation receiver is designed as a stationary detector ring. For scanning only the x-ray tubes are rotated about the radiography subject. They are maintained at such a distance from one another that no detector element is simultaneously impinged upon by both radiation beams.

2 Claims, 2 Drawing Figures

TOMOGRAPHIC APPARATUS FOR THE PRODUCTION OF TRANSVERSE LAYER IMAGES

BACKGROUND OF THE INVENTION

The invention relates to a tomograph for the production of transverse layer images of a radiography subject, comprising an x-ray measuring arrangement which contains two x-ray sources of different radiation energy which generate radiation beams penetrating the radiography subject, the cross-sectional extent of said radiation beams perpendicular to the layer plane being substantially equal to the layer thickness, and also containing a radiation receiver which determines the radiation intensity behind the subject, as well as comprising a rotating device for irradiation of the radiography subject from different directions, and comprising a computer for the determination of the attenuation coefficients of every image point in an image point-matrix disposed in the examined layer, wherein the computer is so designed that it determines, for every image point, the attenuation coefficient for every radiation energy, and determines therefrom the median ordinate value and the density.

A computer tomograph of this type is known in which, for scanning of the subject, there is present, for every radiation source, one radiation receiver which is fixedly connected with the respective radiation source (U.S. Pat. No. 3,971,948). For scanning of the subject, there alternately takes place a common lateral displacement of both radiation sources and both radiation receivers and a rotation of these structural units. In the case of the known tomograph, it is disadvantageous that the technical outlay for the scanning of the radiography subject is very great.

SUMMARY OF THE INVENTION

The object underlying the invention resides in designing a tomographic apparatus of the type initially cited such that the outlay is reduced in relation to the state of the art.

In accordance with the invention, this object is achieved in that the radiation receiver, as a stationary ring, is comprised of a plurality of detector elements, and that, for scanning, only the radiation sources are rotated about the radiography subject, and that the radiation sources are maintained at such a distance from one another that no detector element is simultaneously impinged upon by both radiation beams. In the case of the inventive tomograph, for scanning the radiography subject, only the two radiation sources are rotated about the radiography subject. The radiation receiver, in the form of a detector ring, is stationary. Every radiation source can thus emit a fan-shaped radiation beam whose marginal rays form the marginal rays of the measuring field, so that a lateral displacement for the purpose of scanning the entire layer of which an image is to be formed is not necessary.

The invention shall be explained in greater detail in the following on the basis of an exemplary embodiment illustrated in the accompanying drawing sheet; and other objects, features and advantages will be apparent from this detailed disclosure and from the appended claims.

DETAILED DESCRIPTION

Figure 1:
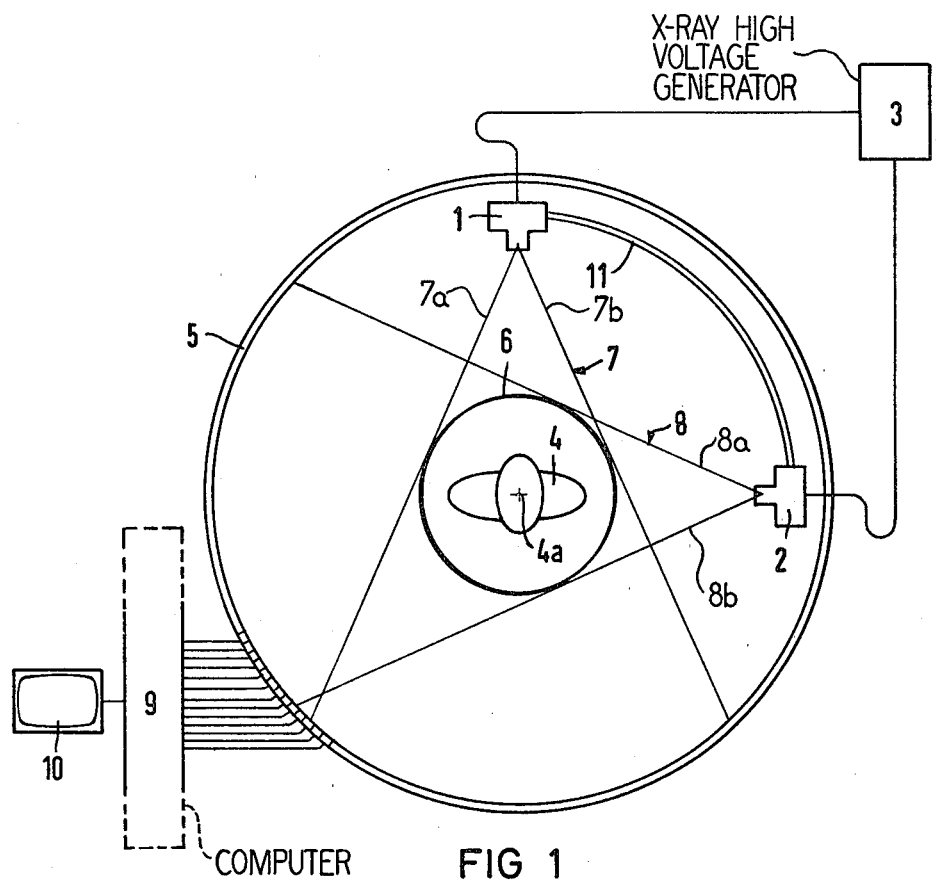
FIG. 1 illustrates a tomographic apparatus in accordance with the invention.

In FIG. 1, two x-ray tubes 1 and 2 are illustrated which are fed by an x-ray high voltage generator 3. The patient 4 is encompassed by a radiation receiver 5 which is comprised of a plurality of detector elements for x-radiation. The radiation receiver 5 receives simultaneously, respectively, two ray fans 7 and 8 traversing (or penetrating) the measuring field 6 and hence traversing a cross-section of the patient 4, the marginal rays 7a, 7b; 8a, 8b of said ray fans 7 and 8 forming the marginal rays of the measuring field 6. The thickness of the ray fans 7 and 8, perpendicularly to the layer plane, is equal to the layer thickness. Every detector element of the radiation receiver 5 is connected to a computer 9 which calculates an image of the irradiated cross-section of the patient 4 from the output signals of the detector elements of the radiation receiver 5 obtained during rotation of the x-ray tubes 1 and 2 about the patient 4; namely, about an axis 4a. The computer 9 effects the reproduction of said image on a display unit 10. The image formation (or production) proceeds in that the computer determines the attenuation coefficients of image points in an image point-matrix disposed in the examined layer of the radiography subject 5.

The x-ray tubes 1 and 2 are supplied with different high voltages and therefore deliver different radiation energies. The computer 9 calculates the attenuation coefficient for every radiation energy and every image point, so that there are present, for every image point, two attenuation coefficients from which the median ordinate value of the material in the image point and the density can be calculated. The entire scanning is terminated when both x-ray tubes 1, 2 have rotated through 360° about the patient 4.

The radiation receiver 5, which is designed as a detector ring, is stationary. By means of a rod 11, the x-ray tubes 1, 2 are maintained at a fixed distance from one another which is so selected that no detector element of the radiation receiver is simultaneously struck (or impinged upon) by the two ray fans 7, 8 or by parts thereof. It is therefore possible, with only one detector system, to simultaneously pick up (detect) two data-sets—required for the reconstruction of two images—with two different effective energies. The two data sets are, indeed, obtained with one scan operation; however, always two different regions of the radiation receiver 5 are irradiated by the two ray fans 7, 8, so that every detector element is not simultaneously, but successively, struck (or impinged upon) by both ray fans 7, 8.

Figure 2:
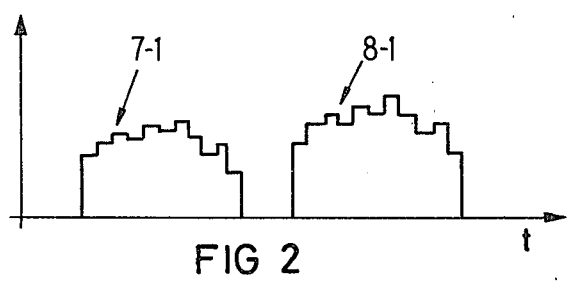
FIG. 2 illustrates a curve for explaining FIG. 1.

The chronological sequence of the measured values recorded by a detector element is illustrated in an example by FIG. 2. One obtains two chronologically separate signals which can be separated prior to the image reconstruction. For example for counterclockwise rotation of sources 1, 2, a given detector might generate successive outputs for successive rotational positions one angular degree apart. After a succession of outputs as indicated at 7-1 for successive angular positions of the rotating sources (due to radiation from source 1), there might be a time interval representing several angular degrees of rotation where neither source was directed toward the detector, after which outputs as indicated at 8-1 would result for successive angular positions of the rotating sources (due to radiation from source 2).

It will be apparent that many modifications and variations may be effected without departing from the scope of the novel concepts and teachings of the present invention.

We claim as our invention:

1. Tomographic apparatus for the production of transverse layer images of a radiography subject, comprising a radiation measuring arrangement having two radiation sources of different radiation energy, which generate radiation beams penetrating the radiography subject, the cross-sectional extent of said radiation beams perpendicular to the layer plane being essentially equal to the layer thickness, and also having a radiation receiver which determines the radiation intensity behind the subject, a rotating device for irradiation of the radiography subject from different directions, and a computer for the determination of the attenuation coefficients of every image point in an image point-matrix disposed in the examined layer, the computer being so designed that, for every image point, it determines the attenuation coefficient for every radiation energy and determines therefrom the median ordinate value and the density, characterized in that the radiation receiver (5), as a stationary ring, is comprised of a plurality of detector elements, and that, for scanning, only the radiation sources (1, 2) are rotated about the radiography subject (4) and that the radiation sources (1, 2) are maintained at such a distance from one another that no detector element is simultaneously impinged upon by both radiation beams (7, 8).

2. Tomographic apparatus according to claim 1, characterized in that every radiation source (1, 2) emits a fan-shaped radiation beam (7, 8) whose marginal rays form the marginal rays of the measuring field (6).

* * * * *